(12) United States Patent
Jost et al.

(10) Patent No.: US 9,365,601 B2
(45) Date of Patent: Jun. 14, 2016

(54) 1,2-CYCLOHEXANEDIAMINPLATINUM(II)-BIS-(4-METHYLBENZENESULFONATE) AND THE HYDRATES THEREOF

(71) Applicant: HERAEUS PRECIOUS METALS GMBH & CO. KG, Hanau (DE)

(72) Inventors: Steffen Jost, Gründau (DE); Christian Brandes, Linsengericht (DE); Holger Rauter, Flieden (DE); Silvia Werner, Kahl (DE); Stefanie Schmengler, Griesheim (DE)

(73) Assignee: HERAEUS DEUTSCHLAND GMBH & CO. KG, Hanau (DE)

( * ) Notice: Subject to any disclaimer, the term of this patent is extended or adjusted under 35 U.S.C. 154(b) by 0 days.

(21) Appl. No.: 14/096,059

(22) Filed: Dec. 4, 2013

(65) Prior Publication Data

US 2014/0187727 A1    Jul. 3, 2014

(30) Foreign Application Priority Data

Dec. 5, 2012   (EP) .................................... 12008120

(51) Int. Cl.
| C07F 15/00 | (2006.01) |
| C08G 69/48 | (2006.01) |
| G01N 30/00 | (2006.01) |
| C08L 33/26 | (2006.01) |

(52) U.S. Cl.
CPC ............ *C07F 15/0093* (2013.01); *C08G 69/48* (2013.01); *G01N 30/00* (2013.01); *C08L 33/26* (2013.01)

(58) Field of Classification Search
CPC .................................................. C07F 15/0093
See application file for complete search history.

(56) References Cited

U.S. PATENT DOCUMENTS

| 4,931,553 | A | 6/1990 | Gill et al. |
| 7,608,730 | B2 | 10/2009 | Maikap et al. |
| 2008/0207935 | A1 | 8/2008 | Maikap et al. |
| 2010/0267824 | A1 | 10/2010 | Sehgal et al. |
| 2011/0286958 | A1 | 11/2011 | Sood et al. |

FOREIGN PATENT DOCUMENTS

| JP | S 60 13795 A | 1/1985 |
| JP | H 03 504859 A | 10/1991 |
| WO | 89 10928 A1 | 11/1989 |
| WO | 2005 075489 A1 | 8/2005 |

OTHER PUBLICATIONS

European Search report for corresponding EP application 12008120.3-1451 dated May 28, 2013.
Schwartz, Paul et al; "Preparation and antitumor evaluation of water-soluble derivatives of dichloro(1,2-diaminocyclohexane) platinum(II)"; Cancer Treatment Reports, vol. 61, No. 8; Nov. 1, 1977, pp. 1519-1525.
European Pharmacopeia Commission et al; "Oxaliplatin"; European Pharmacopoeia 7.3; Jun. 1, 2011; pp. 3988-3990.
English translation of JP Office Action mailed Oct. 14, 2014.

*Primary Examiner* — Sudhakar Katakam
(74) *Attorney, Agent, or Firm* — Norris McLaughlin & Marcus, P.A.

(57) ABSTRACT

The present invention describes the dihydrate of 1,2-cyclohexanediaminplatinum(II)-bis-(4-methylbenzenesulfonate), a method for producing 1,2-cyclohexanediaminplatinum(II)-bis-(4-methylbenzenesulfonate) and the hydrates thereof, and the use of 1,2-cyclohexanediaminplatinum(II)-bis-(4-methylbenzenesulfonate) and of the hydrates thereof.

15 Claims, 4 Drawing Sheets

1,2-CYCLOHEXANEDIAMINPLATINUM(II)-BIS-(4-METHYLBENZENESULFONATE) AND THE HYDRATES THEREOF

This application claims priority of European Patent Application No. 12 008 120.3, filed on Dec. 5, 2012, the entire contents of which is incorporated herein by reference.

The present invention relates to the dihydrate of 1,2-cyclohexanediaminplatinum(II)-bis-(4-methylbenzenesulfonate), a method for producing 1,2-cyclohexanediaminplatinum(II)-bis-(4-methylbenzenesulfonate) and the hydrates thereof, and the use of 1,2-cyclohexanediaminplatinum(II)-bis-(4-methylbenzenesulfonate) and of the hydrates thereof.

Ever since the discovery of the cytostatic effect of cisplatin (diaminodichloroplatinum), platinum complexes have played an important role in the research and development of anti-tumour agents. The effect of said platinum complexes is based on the inhibition of DNA replication by cross-links between two adjacent guanine bases of one DNA strand. This disturbs the structure of the DNA and renders it non-functional. Consequently, cellular metabolism is arrested and the cell initiates apoptosis.

Said platinum complexes with a cytostatic effect usually comprise two stable ligands and two non-stable ligands, which are cleaved off in the course of a reaction. Inside the body, the platinum complexes react with water cleaving off the non-stable ligands. The aqua complexes thus obtained then react with the DNA inside the cell and thus lead to death of the cell.

The aim of the continued development of platinum complexes is, firstly, the stability of said complexes with respect to water such that the aqua complexes only form inside the human body and not earlier, during production or storage. Moreover, the agent should act as selectively as possible in tumour tissue and should not attack healthy cells that are not afflicted by the tumour.

Oxaliplatin is a recent platinum complex with a cytostatic effect (oxalato[(1R,2R)-cyclohexanediamin]platinum(II)), in which the platinum ion is complexed by a 1,2-diaminocyclohexyl ligand (DACH ligand) and an oxalate ion. Compared to cisplatin, oxaliplatin shows improved properties, in particular in terms of its stability. However, even in this case reactions proceed during storage, in the course of which oxaliplatin is degraded resulting in the concentration of the agent being reduced and impurities accumulating. According to the European Pharmacopoeia, oxaliplatin is known to be associated with impurities A, B, C, D, and E. These are usually called "impurity".

"Impurity A" is oxalic acid, which is produced during the hydrolysis of oxaliplatin. Another impurity produced during hydrolysis is (SP-4-2)-diaqua[(1R,2R)-cyclohexane-1,2-diamin-κN, κN']platinum (diaquodiaminocyclohexaneplatinum), which is referred to as "impurity B".

The product of oxaliplatin oxidation, (OC-6-33)-[(1R,2R)-cyclohexane-1,2-diamin-κN, κN'][ethane-dioato(2-)κO1, κO2]dihydroplatinum is referred to as "impurity C". "Impurity D" is (SP-4-2)-[(1S,2S)-cyclohexane-1,2-diamin-κN, κN'][ethanedioato(2-)-κO1, κO2]platinum and "impurity E" is (SP-4-2)-di-g-oxobis[(1R,2R)-cyclohexane-1,2-diamine-κN, κN']diplatinum. Moreover, further impurities are known, but are present in very small amounts only.

In order to keep the amount of impurities produced low or eliminate them altogether, US 2010/0267824 A1 proposes a pH range from 3 to 4.5 for an oxaliplatin compound for parenteral intake. This can reduce the fraction of impurities, but not eliminate them altogether.

The European Pharmacopoeia defines reference standards for the determination of the fraction of impurities. Currently, dinitrato(1,2-diaminocyclohexane)platinum(II) is used as reference standard for impurity B. This substance forms a reactive diaminocyclohexanediaquaplatinum(II) complex in water. Surprisingly, it has been found that dinitrato(1,2-diaminocyclohexane)platinum(II) is an explosive substance, which makes its transport, storage, and handling difficult. FIG. 1 shows a differential thermal analysis (DTA measurement) of dinitrato(1,2-diaminocyclohexane)platinum(II) (Pt (DACH)($NO_3$)$_2$), to evidence the tendency to explode. Two samples Mz1 Mz2 of Pt(DACH)($NO_3$)$_2$ were subjected to the measurement. Each of the samples was heated at a heating rate of 3K/min from room temperature to 450° C. inside a closed glass ampoule filled with nitrogen. The temperature difference between the platinum compound Pt(DACH) ($NO_3$)$_2$ and a reference sample ($Al_2O_3$) was recorded. Both samples showed the start of exothermic behaviour at 170° C. at a heat tone of 1.175 J/g. The measurement was carried out in accordance with guideline VDI 2263.

Accordingly, there is a need for a (1,2-diaminocyclohexane)platinum(II) compound that forms a reactive diaminocyclohexanediaquaplatinum(II) complex without being explosive.

Schwartz et al. (Preparation and Antitumor Evaluation of Water-Soluble Derivatives of Dichloro(1,2-diaminocyclohexane)platinum(II), Cancer Treatment Reports Vol. 61, No. 8, November 1977, 1519-1525) describe a monohydrate of 1,2-cyclohexanediaminplatinum(II)-bis-(4-methylbenzenesulfonate). Said substance forms the desired reactive diaqua complex in water. The solubility in water of the monohydrate of 1,2-cyclohexanediaminplatinum(II)-bis-(4-methylbenzenesulfonate) is 3 mg/ml. The solubility was also improved from that of dinitrato(1,2-diaminocyclohexane)platinum(II), which is thus far being used as standard and has a solubility in water of approx. 0.5 mg/ml. Further improvement of the solubility would be desirable though.

The publication of Schwartz et al. (dito) describes a method for producing the monohydrate of 1,2-cyclohexanediaminplatinum(II)-bis-(4-methylbenzenesulfonate). The solvent, water, is evaporated in this method. Consequently, the crystallisation of the product can virtually not be controlled. The isolation of the product is effected through mechanical means. This would be a problem in large-scale production of the product, because large amounts of a firm crust would have to be scraped off. This might also be hazardous for the personnel in charge since mechanical isolation is associated with dusts and fine particles arising which might be inhaled.

The form obtained should possess good solubility in water and be easy to handle altogether. This is to circumvent the disadvantageous properties of dinitrato(1,2-diaminocyclohexane)platinum(II).

Another crucial actor of anti-tumour agents, aside from the stability, is that these should act specifically on the afflicted tissue. For this purpose, polymers or target molecules can be bound to the platinum complex. Pertinent polymers and target molecules are described, for example, in US 2011/0286958 A1. The polymers substitute for the non-stable ligands of the platinum complex. The starting material used for binding the polymers to a platinum complex is dinitrato(1,2-diaminocyclohexane)platinum(II). This substance is poorly water-soluble though. Moreover, as mentioned above, it is an explosive substance such that its production, transport, storage, and handling are difficult.

Therefore, according to a first aspect, the objective of the invention is to provide a compound that is an alternative to dinitrato(1,2-diaminocyclohexane)platinum(II) and possesses comparatively better solubility. Moreover, the compound should be stable and easy to handle. Moreover, it should also be suitable for use as reference standard for impurity B of oxaliplatin.

Therefore, another aspect of the present invention is to provide a method for producing a compound that can be used as an alternative to dinitrato(1,2-diaminocyclohexane)platinum(II) and overcomes the disadvantages mentioned above. The compound obtained from the method is also to be suitable for use as reference standard for impurity B of oxaliplatin. Moreover, the compound should be suitable for use as an alternative starting substance replacing dinitrato(1,2-diaminocyclohexane)platinum(II) in the synthesis of polymer-bound cyclohexanediamino-platinum(II) complexes.

BRIEF DESCRIPTION OF THE DRAWINGS

The invention will now be described in greater detail with reference to the drawings, wherein.

Surprisingly, it has been evident that the objective according to the first aspect of the present invention is met by the dihydrate of 1,2-cyclohexanediaminplatinum(II)-bis-(4-methylbenzenesulfonate). The solubility in water of the dihydrate at a temperature of 25° C. and normal pressure is approx. 90 mg/ml. Accordingly, the solubility in water was improved markedly as compared to the monohydrate that is known according to the prior art and has a solubility in water of approx. 3 mg/ml at the same conditions.

The dihydrate of 1,2-cyclohexanediaminplatinum(II)-bis-(4-methylbenzenesulfonate) is preferably present in the form of crystals. These are analysed by means of X-ray powder diffractometry (XRPD) (FIG. 2) and dynamic differential scanning calorimetry (DSC) (FIG. 3).

Figure 2:
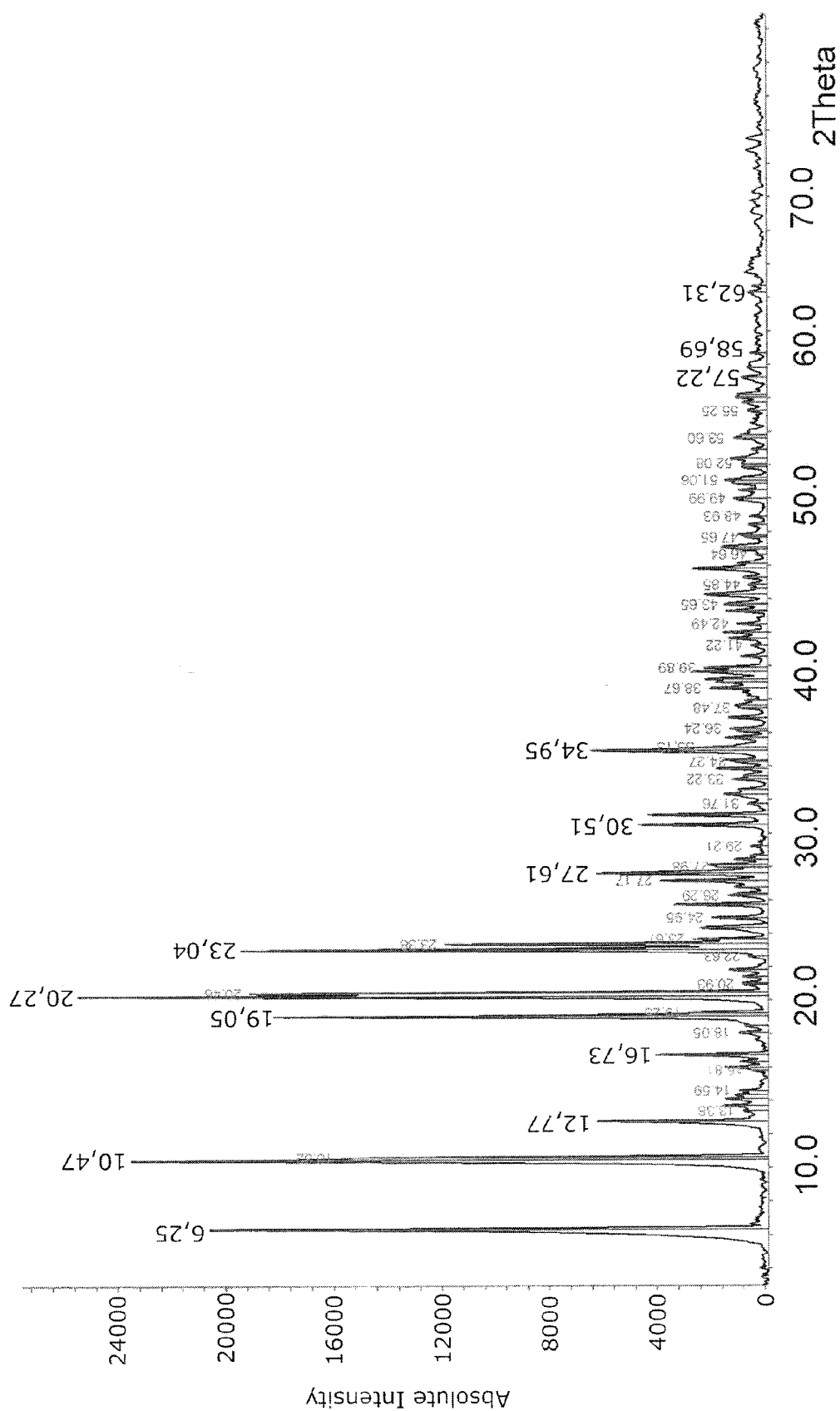
FIG. 2 is a X-ray powder diffractometry (XRPD) of crystals of the dihydrate of 1,2-cyclohexanediaminplatinum(II)-bis-(4-methylbenzenesulfonate)
Figure 3:
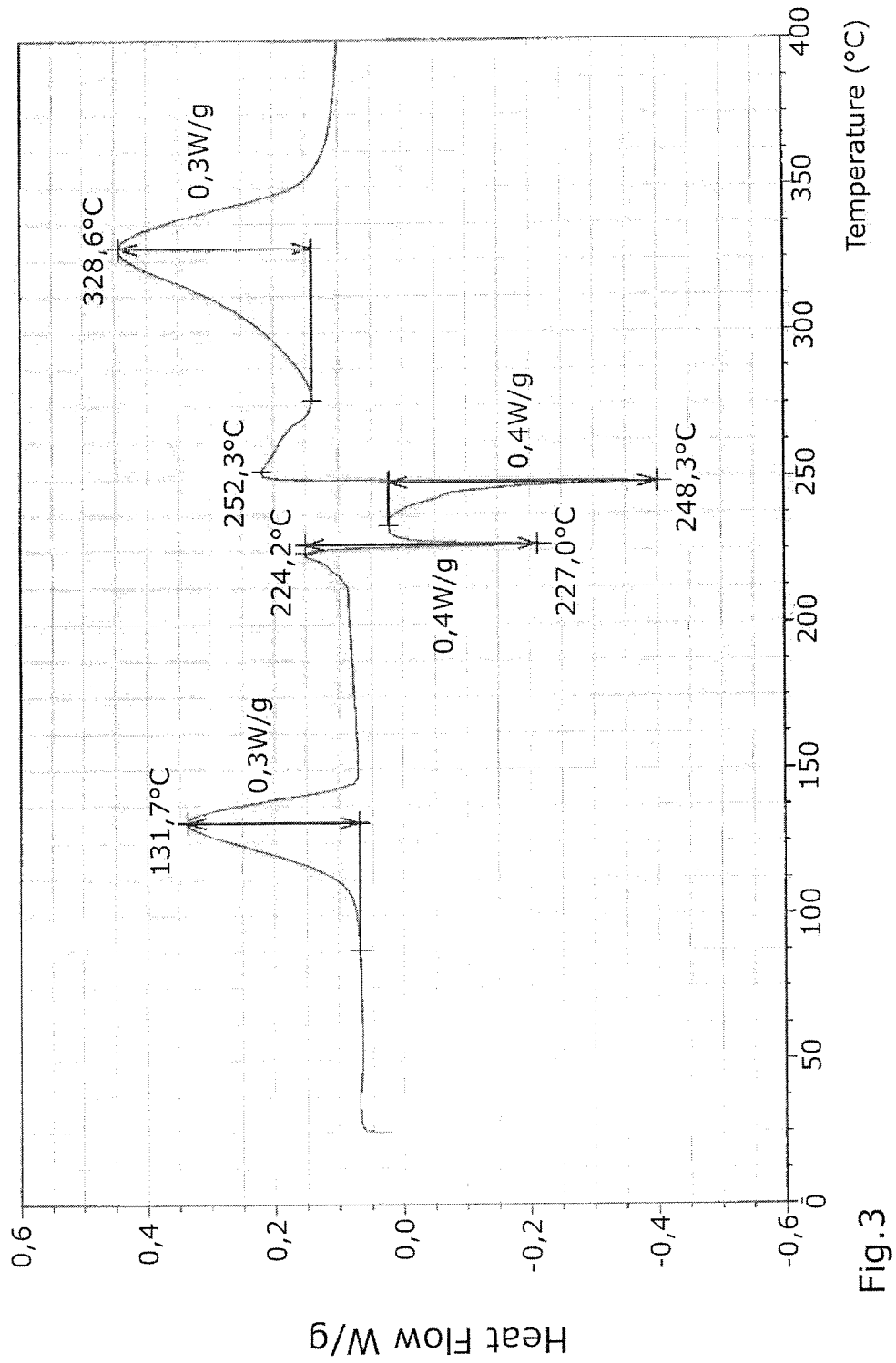
FIG. 3 is a dynamic differential scanning calorimetry (DSC) of crystals of the dihydrate of 1,2-cyclohexanediaminplatinum(II)-bis-(4-methylbenzenesulfonate) is preferably present in the form of crystals.

The X-ray powder diffractogram in FIG. 2 shows typical signal positions of the crystalline material at 2theta (2θ) values of 6.35±0.2, 10.47±0.2, 10.62±0.2, 12.77±0.2, 19.05±0.2, 20.27±0.2, 20.40±0.2, 23.04±0.2, 23.38±0.2, 27.61±0.2, 30.51±0.2, and 34.95±0.2. The error margin is due to known uncertainties in the XRPD measurement, such as residual amounts of solvent being present in the sample. FIG. 2 shows both the discrete signal peaks and the spectrum of the dihydrate of 1,2-cyclohexanediaminplatinum(II)-bis-(4-methylbenzenesulfonate). The XRPD spectra are preferably recorded in a Stadi P powder diffraction system made by Stoe (Darmstadt, Germany) using Cu K☐$_1$ radiation (1.54056 Angström=0.154056 nm). The measurement is preferably done in transmission using a curved Ge monochromator (111) and an IP-PSD detector (imaging plate position-sensitive detector) at an X-ray tube generator voltage of 40 kV and 30 mA. Preferably, the sample is introduced at a fixed angle omega of 40°, whereby omega is the orientation of the sample or specimen holder with respect to the primary X-ray beam during the measurement. It is preferable to measure over a 2theta scanning range of 3.0° to 79.05°.

The DSC spectrum (FIG. 3) shows a number of endo- and exothermic signals that are related to the release of water or phase transitions. The sample measured consisted of 11.550 mg of the dihydrate of 1,2-cyclohexanediaminplatinum(II)-bis-(4-methylbenzenesulfonate). However, there are no peaks recognisable that would be indicative of explosive decomposition, as is the case with $Pt(DACH)(NO_3)_2$. The DSC recordings are preferably made using a DSC Q2000 made by TA Instruments (New Castle, Del., USA). Preferably, the sample is equilibrated at 25° C. and the measurement is done using a temperature ramp of 2° C. up to a temperature of 400° C.

Both techniques (XRPD and DSC) are well-established measuring methods of the prior art.

Moreover, the dihydrate of 1,2-cyclohexanediaminplatinum(II)-bis-(4-methylbenzenesulfonate) surprisingly is thermodynamically more stable than the monohydrate of 1,2-cyclohexanediaminplatinum(II)-bis-(4-methylbenzenesulfonate).

In water, the dihydrate of 1,2-cyclohexanediaminplatinum(II)-bis-(4-methylbenzenesulfonate) forms a reactive diaminocyclohexanediaquaplatinum(II) complex. Accordingly, a 1,2-cyclohexanediaminodiaquaplatinum(II)-bis-(4-methylbenzenesulfonate) complex is present in the dissolved state. The compound according to the invention can take various forms in the solid state. In this context, it is feasible that not only the diaminocyclohexane (DACH) group, but also both tosylate groups (4-methylbenenesulfonate groups) are bound to the central platinum(II) atom by coordination. Moreover, two water molecules can also be bound to the platinum(II) atom by coordination in the solid state or a mixed form may be present, in which a tosylate molecule and a water molecule are bound to the platinum(II) atom by coordination.

The dihydrate of 1,2-cyclohexanediaminplatinum(II)-bis-(4-methylbenzenesulfonate) according to the invention possesses clearly improved solubility in water of more than 80 mg/ml as compared to the monohydrate complex that is known from the prior art. Dinitrato(1,2-diaminocyclohexane)platinum(II), which has been described at length in the prior art, also possesses markedly poorer solubility of only approx. 0.5 mg/ml as compared to the compound according to the invention. Solubility, as used in the scope of the present invention, shall be the solubility at room temperature and normal pressure. This is also referred to as solubility at standard conditions in the present application. Moreover, the dihydrate of 1,2-cyclohexanediaminplatinum(II)-bis-(4-methylbenzenesulfonate) according to the invention is a non-explosive compound which is evident from the DSC spectrum appended hereto as FIG. 3. Moreover, this compound can be present in a defined crystal form which can be demonstrated by means of the x-ray powder diffractogram appended hereto as FIG. 2.

According to the further aspect of the present application, the present invention provides a method for producing a compound as an alternative to dinitrato(1,2-diaminocyclohexane)platinum(II), which comprises the following steps in the order given:

a) reacting 1,2-cyclohexanediamindihalogenplatinum(II) and silver 4-methylbenzenesulfonate in a water-containing solvent to form 1,2-cyclohexanediaminplatinum(II)-bis-(4-methylbenzenesulfonate) and silver halogenide;

b) separating the silver halogenide from the reaction mixture from step a);

c) adding a compound that forms an azeotropic mixture with water;

d) removing at least part of the water from the azeotropic mixture;

e) adjusting the water fraction to form the desired hydrate of 1,2-cyclohexanediaminplatinum(II)-bis-(4-methylbenzenesulfonate); and f) isolating 1,2-cyclohexanediaminplatinum(II)-bis-(4-methylbenzenesulfonate) or the hydrate of 1,2-cyclohexanediaminplatinum(II)-bis-(4-methylbenzenesulfonate).

The method according to the invention enables the production of the monohydrate of 1,2-cyclohexanediaminplatinum(II)-bis-(4-methylbenzenesulfonate), which has already been described by Schwartz et al. (dito). In contrast to the production method described in said reference, the solvent is not evaporated in uncontrolled manner. This enables controlled crystallisation of the desired product. The method according to the invention also enables production of the desired product at larger scale. There is no associated hazard for people involved in production.

Moreover, it is also feasible to produce not only the monohydrate, but also the dihydrate of 1,2-cyclohexanediaminplatinum(II)-bis-(4-methylbenzenesulfonate) or further hydrates thereof. The method also enables the production of the non-hydrated platinum complex, 1,2-cyclohexanediaminplatinum(II)-bis-(4-methylbenzenesulfonate). Accordingly, the present invention provides a method for producing 1,2-cyclohexanediaminplatinum(II)-bis-(4-methylbenzenesulfonate) and hydrates thereof that overcomes the disadvantages known from the prior art.

The halogen atoms in the basic substance, 1,2-cyclohexanediaminodihalogenplatinum(II), that is present in step a) can be any halogen atoms. Chlorine (Cl), bromine (Br) and/or iodine (I) are preferred. The platinum(II) complex that is used in this context can contain two identical or two different halogen ligands. Preferably, two identical halogen ligands are situated on the platinum(II) complex since this allows an unambiguous stoichiometry in the reaction with the silver salt to be determined. Accordingly, it is preferable to use 1,2-cyclohexanediamindibromoplatinum(II)-bis-(4-methylbenzenesulfonate), 1,2-cyclohexanediamindichloroplatinum(II)-bis-(4-methylbenzenesulfonate) or 1,2-cyclohexanediamindiiodoplatinum(II)-bis-(4-methylbenzenesulfonate) as educt in step a) of the method according to the invention.

The reaction of 1,2-cyclohexanediamindihalogenplatinum(II) and silver 4-methylbenzenesulfonate in step a) proceeds in a water-containing solvent. Preferably, said solvent is water or a mixture containing water and at least one further compound that forms an azeotropic mixture with water. In this context, it is feasible to mix the water with multiple different compounds. The compounds must be miscible with water at defined ratios and must form an azeotropic mixture with water. According to the invention, it is also feasible to mix just one compound with water and thereby form the azeotropic mixture.

The reaction of 1,2-cyclohexanediamindihalogenplatinum(II) complexes and silver 4-methylbenzenesulfonate in step a) preferably proceeds at sub-stoichiometric levels of silver 4-methylbenzenesulfonate. Accordingly, the platinum complex is reacted with less than two molar equivalents of silver salt in the synthesis. A preferred amount of silver 4-methylbenzenesulfonate is in the range of 1.88 to 1.99 molar equivalents, particularly preferable is an amount in the range of 1.92 to 1.96 molar equivalents. The reaction of the two components produces 1,2-cyclohexanediaminplatinum(II)-bis-(4-methylbenzenesulfonate) and silver halogenide. The reaction proceeds in a water-containing solvent. The resulting silver halogenides are only very poorly soluble in said solvent and thus precipitate. The corresponding precipitate can thus be separated easily from the rest of the reaction mixture, preferably by means of filtration. Using a sub-stoichiometric amount of silver 4-methylbenzenesulfonate in the reaction prevents silver from being present in the final product. This would render separation difficult. The fraction of silver 4-methylbenzenesulfonate must not be too low though, because otherwise only a small fraction of 1,2-cyclohexanedihalogenplatinum(II) would react with the tosylate group and the yield of the desired product (1,2-cyclohexanediaminplatinum(II)-bis-(4-methylbenzenesulfonate) and hydrates thereof) would be low.

In order to absorb side products or unconverted educts, it is feasible to add activated charcoal to the reaction mixture in step c) after separation of the silver halogenide in step b) of the method according to the invention and before the addition of the compound that forms an azeotropic mixture with water. If the reaction proceeds according to a preferred embodiment, i.e. with substoichiometric levels, the activated charcoal removes, in particular, unreacted 1,2-cyclohexanedihalogenplatinum(II) from the reaction mixture. Besides, the activated charcoal also removes silver salts and side products.

Preferably, the fraction of activated charcoal to be added is from 1% by weight to 20% by weight, particularly preferably from 2% by weight to 10% by weight, even more particularly preferably from 3% by weight to 7% by weight, yet more preferably 5% by weight, with respect to the platinum(II) compound used. Said amount is sufficient for removing the existing unreacted educts and side products from the reaction mixture.

After separation of the silver halogenide, at least one compound forming an azeotropic mixture with water is added in step c) of the method according to the invention. In this context, it is feasible to add one compound to the reaction mixture. It is also feasible according to the invention to add multiple compounds that form an azeotropic mixture with water in step c) of the method. The at least one compound is preferably selected from the group comprising alcohols and halogenated hydrocarbons. These form an azeotropic mixture with water. Moreover, the solubility of 1,2-cyclohexanediaminplatinum(II)-bis-(4-methylbenzenesulfonate) and hydrates thereof in said compounds is particularly high. Preferably, the solubility of the platinum(II) compound is 5 g/l or more, particularly preferably 7 g/l or more, at standard conditions (room temperature, normal pressure). Particularly preferably, the compound is selected from the group comprising n-butanol, toluene, chloroform, and ethanol. A mixture containing water and the compound according to the invention can just as well be used as water-containing solvent in step a) of the method according to the invention.

It is preferred to add just one compound to the reaction mixture, preferably one selected from the group comprising alcohols or halogenated hydrocarbons, particularly preferably from the group comprising n-butanol, toluene, chloroform, and ethanol. In a particularly preferred embodiment, n-butanol is added to the reaction mixture in step c) of the method according to the invention. It is preferred to use n-butanol since the boiling point of the azeotropic mixture made up of n-butanol and water is 92° C. and as such is favourable for the subsequent steps of the method according to the invention. Moreover, the product obtained in said step, 1,2-cyclohexanediaminplatinum(II)-bis-(4-methylbenzenesulfonate), is quite soluble in n-butanol, which simplifies the further purification of the product and enables a high yield to be obtained.

Subsequently, at least part of the water is removed from the azeotropic mixture thus formed. This can be done using methods that are known according to the prior art. Preferably, the water is removed by azeotropic distillation. It is particularly preferable to remove the water not only partly, but fully, from the azeotropic mixture in step d) of the method according to the invention. As a result, the compound forming an azeotropic mixture with water is obtained. 1,2-Cyclohexanediaminplatinum(II)-bis-(4-methylbenzenesulfonate) and hydrates thereof are soluble in said compound.

After at least partial removal of the water from the azeotropic mixture follows the adjustment of the fraction of water needed for formation of the desired hydrate of 1,2-cyclohexanediaminplatinum(II)-bis-(4-methylbenzenesulfonate). The water fraction that is needed can be calculated by stoichiometry. If the method according to the invention is to lead to the non-hydrated form of 1,2-cyclohexanediaminplatinum(II)-bis-(4-methylbenzenesulfonate), no water is added here. In order to obtain a hydrate of the compound, the amount of water needed can be calculated and admixed to the reaction mixture. Preferably, the water fraction is adjusted appropriately in step e) of the method according to the invention such that the dihydrate of 1,2-cyclohexanediaminplatinum(II)-bis-(4-methylbenzenesulfonate) is obtained and said substance is then removed in step f) of the method according to the invention.

The product can be isolated in step f) according to methods that are known from the prior art. Preferably, an anti-solvent is added to the reaction mixture in order to isolate 1,2-cyclohexanediaminplatinum(II)-bis-(4-methylbenzenesulfonate) or the hydrate of 1,2-cyclohexanediaminplatinum(II)-bis-(4-methylbenzenesulfonate). The desired product possesses low solubility in the anti-solvent of preferably less than 2 g/l, in particular of less than 1 g/l at standard conditions (room temperature, normal pressure). Concurrently, the anti-solvent possesses high solubility in the compound that forms an azeotropic mixture with water. High solubility in the scope of the invention shall be understood to preferably mean unlimited miscibility of the anti-solvent in the compound that forms an azeotropic mixture with water at any ratio while forming a homogeneous phase. According to the invention, an anti-solvent can be used alone or multiple compounds can be mixed with each other and used as anti-solvent.

It is preferable to use ethyl acetate and/or acetone as anti-solvent in the method according to the invention. Ethyl acetate is particularly preferred as the anti-solvent, in particular if n-butanol is the compound that forms an azeotropic mixture with water. Ethyl acetate and n-butanol are well-miscible with each other. Concurrently, the desired product, 1,2-cyclohexanediaminplatinum(II)-bis-(4-methylbenzenesulfonate) or the hydrates thereof, are soluble in n-butanol, but not in ethyl acetate.

It is feasible to re-crystallise the compound thus obtained to purify it further. For this purpose, the compound is dissolved in the compound that forms an azeotropic mixture with water. Adding the anti-solvent allows, preferably, crystals of the desired compound to be obtained.

In a particular embodiment, the present invention therefore comprises a method for producing 1,2-cyclohexanediaminplatinum(II)-bis-(4-methylbenzenesulfonate) and the hydrates thereof comprising the following steps:
a) reacting 1,2-cyclohexanediamindihalogenplatinum(II), whereby the two halogens are identical and are selected from chlorine, bromine or iodine, and silver 4-methylbenzenesulfonate, whereby the silver 4-methylbenzenesulfonate is present in sub-stoichiometric amounts with respect to the platinum(II) compound, in a water-containing solvent while forming 1,2-cyclohexanediaminplatinum(II)-bis-(4-methylbenzenesulfonate) and silver halogenide;
b) separating the silver halogenide from the reaction mixture from step a), and subsequently adding activated charcoal to the reaction mixture;
c) adding n-butanol;
d) removing all of the water from the azeotropic mixture by means of azeotropic distillation;
e) adjusting the water fraction to form the dihydrate of 1,2-cyclohexanediaminplatinum(II)-bis-(4-methylbenzenesulfonate); and
f) isolating the dihydrate of 1,2-cyclohexanediaminplatinum(II)-bis-(4-methylbenzenesulfonate) by adding ethyl acetate as anti-solvent.

Adding the anti-solvent preferably ensures that the crystallisation of the product proceeds as preferred, slowly and in controlled manner. This allows uncontrolled crystallisation, which is common when the solvent is evaporated, to be prevented. Accordingly, the method according to the invention can be used to obtain a crystalline compound of defined composition. Controlled production according to the method according to the invention, in particular, enables the use as reference standard since a clearly defined substance must be available for this purpose.

The European Pharmacopoeia EP 7.3 currently specifies the compound, 1,2-cyclo-hexanediamindinitratoplatinum(II) (=dinitrato(1,2-diaminocyclohexane)-platinum(II)) as reference standard for impurity B of oxaliplatin. Its use is described as follows:

For use as a reference standard, dissolve 5 mg of oxaliplatin impurity B CRS (CRS=current reference standard) in 25 methanol and fill the container up to 100 ml with water. Sonicate the solution for 1.5 h until the solution is clear. For analysis, dissolve 100 mg of the oxaliplatin agent in water and fill the container up to 50 ml.

Both solutions are subsequently injected one after the other into an HPLC system (column I=0.25 m; diameter=4.6 mm; stationary phase: base-deactivated octadecylsilyl silica gel 5 μm). The measuring temperature is 40° C. The mobile Phase consists of 20% acetonitrile and 80% of an aqueous solution containing 1.36 potassium hydrogenphosphate and 1 g sodium heptanesulfonate in 1,000 ml water, pH adjusted to 3.0±0.05 with phosphoric acid. Measuring conditions: flow rate 2.0 mL/min., detection: spectrophotometer at 215 nm, injection volume: 20 μL.

The fraction of impurity B in the oxaliplatin agent is calculated from the ratio of the percentage area in the respective HPLC chromatograms.

The disadvantages of the use of 1,2-cyclohexanediamindinitratoplatinum(II) as standard for impurity B ((SP-4-2)-diaqua[(1R,2R)-cyclohexane-1,2-diamin-κN, κN']platinum) include its explosiveness and the poor solubility in water.

Surprisingly, it has been evident that the reference standard can be replaced, which overcomes the disadvantages specified above. The use, according to the invention, of 1,2-cyclohexanediaminplatinum(II)-bis-(4-methylbenzenesulfonate) and hydrates thereof as reference standard for impurity B of oxaliplatin therefore comprises
i. providing an oxaliplatin solution;
ii. providing a solution of 1,2-cyclohexanediaminplatinum(II)-bis-(4-methylbenzenesulfonate) or hydrates thereof as reference standard;
iii. recording a chromatogram of the oxaliplatin solution from step i);
iv. recording a chromatogram of the reference standard solution from step ii); and
v. comparing the chromatograms from steps iii) and iv) in order to determine the fraction of (SP-4-2)-diaqua[(1R, 2R)-cyclohexane-1,2-diamin-κN, κN']platinum.

Figure 1:
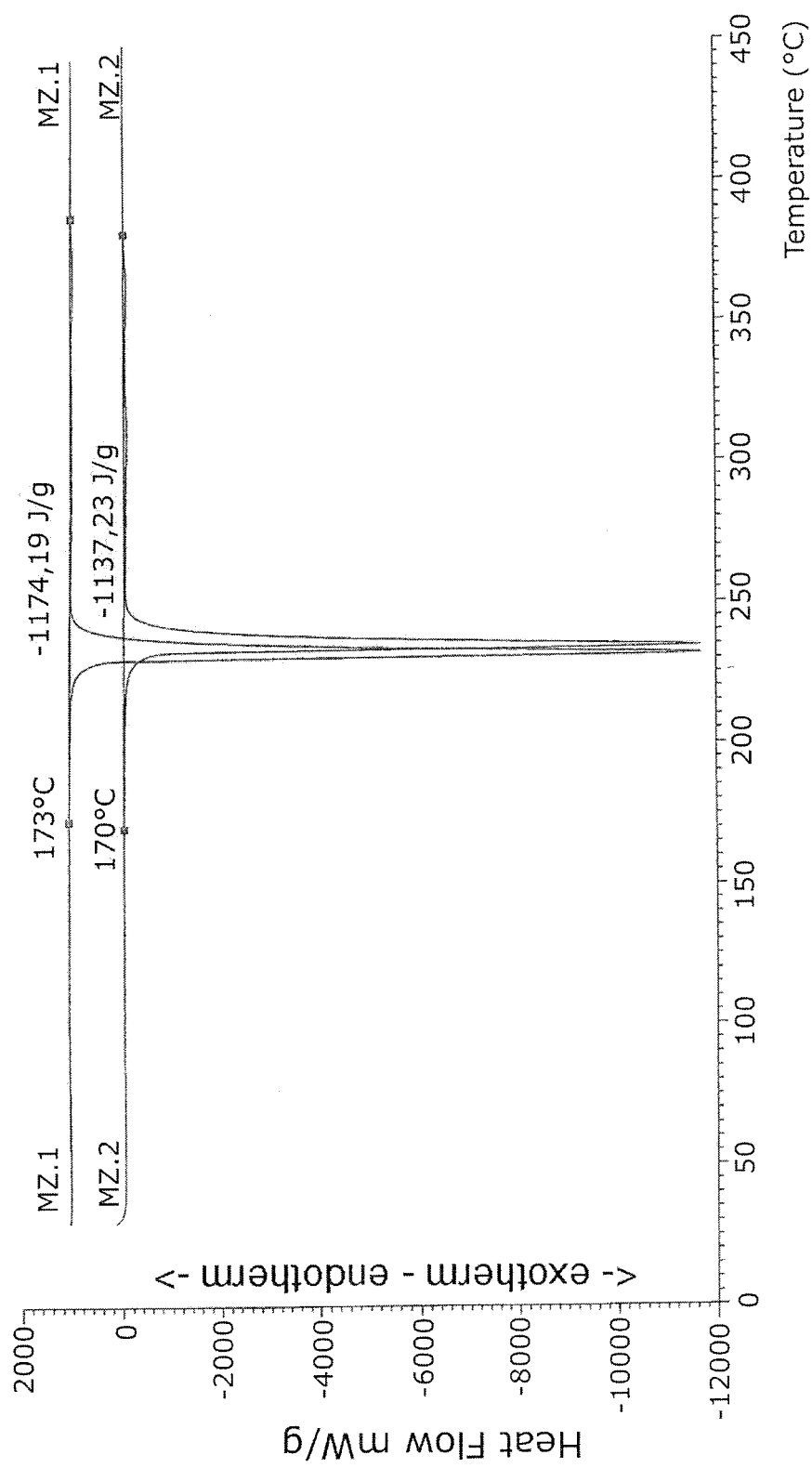
FIG. 1 shows a differential thermal analysis (DTA measurement) of dinitrato(1,2-diaminocyclohexane)platinum(II) ($Pt(DACH)(NO_3)_2$), to evidence the tendency to explode.

In a frequently used method for oxaliplatin synthesis, the substance, dinitrato(1,2-diaminocyclohexane)platinum(II), is produced as a side product. Said substance is therefore used according to the prior art as reference standard for impurity B, (SP-4-2)-diaqua[(1R,2R)-cyclohexane-1,2-diamin-κN, κN'] platinum. However, it has been evident that said substance can explode when exposed to heat as is evident from the DTA measurement appended as FIG. 1. 1,2-Cyclohexanediaminplatinum(II)-bis-(4-methylbenzenesulfonate), used according to the invention, does not show said tendency to explode. The hydrates that can be used according to the invention are also thermally stable as is evident, for the case of the dihydrate, from the appended DSC spectrum (FIG. 3). Moreover, using the method according to the invention allows products to be obtained that crystallise in controlled manner and which have a clearly defined composition. Accordingly, the concentration of the solution in step ii) can be adjusted in reproducible manner.

It is preferable to use an aqueous solution of oxaliplatin and also an aqueous solution of 1,2-cyclohexanediaminplatinum(II)-bis-(4-methylbenzenesulfonate) or of the hydrates thereof. In this context, the compound according to the invention has an additional advantage, as compared to the dinitrato compound known from the prior art, in that is possesses better solubility in water. Accordingly, it is also feasible to provide more concentrated solutions as reference standard.

In order to determine the fraction of impurity B in oxaliplatin, it is feasible, for example, to produce an aqueous solution of oxaliplatin at a concentration of 2 mg/ml in water. An aqueous solution of 1,2-cyclohexanediaminplatinum(II)-bis-(4-methylbenzenesulfonate) or hydrates thereof is used as reference standard. Said solution can have a concentration of 0.05 mg/ml.

In a preferred embodiment, the dihydrate of 1,2-cyclohexanediaminplatinum(II)-bis-(4-methylbenzenesulfonate) is used as reference standard. The solubility of the dihydrate in water is 80 mg/ml or more. Accordingly, different reference standards can be provided easily.

In the further course, chromatograms of the oxaliplatin solution and then of the reference standard solution are recorded. A comparison of the chromatograms allows the fraction of impurity B in oxaliplatin to be determined.

Preferably, the chromatograms of the oxaliplatin solution and reference standard solution will be chromatograms from high-pressure liquid chromatography (HPLC). HPLC is a sufficiently well-known chromatographic method. Comparison of the areas of the signals peaks present in the chromatogram allows conclusions to be made concerning the fractions of impurities that are present in oxaliplatin.

In a preferred embodiment, the present invention therefore relates to the use of the dihydrate of 1,2-cyclohexanediaminplatinum(II)-bis-(4-methylbenzenesulfonate) as reference standard for the determination of impurity B of oxaliplatin. Said use comprises:
  i. providing an aqueous oxaliplatin solution;
  ii. providing an aqueous solution of the dihydrate of 1,2-cyclohexanediaminplatinum(II)-bis-(4-methylbenzenesulfonate) as reference standard;
  iii. recording an HPLC chromatogram of the oxaliplatin solution from step i);
  iv. recording an HPLC chromatogram of the reference standard solution from step ii); and
  v. comparing the chromatograms from steps c) and d) in order to determine the fraction of (SP-4-2)-diaqua[(1R, 2R)-cyclohexane-1,2-diamin-κN, κN']platinum.

Due to the good solubility of 1,2-cyclohexanediaminplatinum(II)-bis-(4-methylbenzenesulfonate) and hydrates thereof, in particular of the dihydrate, in water, the reference standard solution is easy to prepare. Referring to the determination of the fraction of impurity B in oxaliplatin, if one uses the amounts and/or concentrations of agent and reference standard specified in the European Pharmacopoeia EP 7.3 and replaces the previous standard by the dihydrate of 1,2-cyclohexanediaminplatinum(II)-bis-(4-methylbenzenesulfonate), a correction factor needs to be taken into consideration in the comparison of areas in the HPLC chromatograms. Said correction factor results from the molar mass ratio of the current standard for impurity B (1,2-cyclohexanediaminodinitratoplatinum(II)) and the reference standard used according to the invention (1,2-cyclohexanediaminplatinum(II)-bis-(4-methylbenzenesulfonate) or hydrates thereof). Using the dihydrate of 1,2-cyclohexanediaminplatinum(II)-bis-(4-methylbenzenesulfonate) as reference standard, the resulting correction factor is (687.69 g/mol)/(433.29 g/mol)=1.587. The ratio of areas (area in the chromatogram of the agent/area in the chromatogram of the reference standard) must be multiplied by this value.

Alternatively, it is feasible just as well to adjust the amount of the new reference standard, i.e. added dihydrate of 1,2-cyclohexanediaminplatinum(II)-bis-(4-methylbenzenesulfonate), by means of a correction factor. If the amount of standard used according to the current specification in the European Pharmacopoeia EP 7.3 is multiplied by the correction factor, the areas in the chromatograms can be compared directly, provided the weighed amounts of oxaliplatin are kept unchanged.

If the monohydrate, any other hydrate or the non-hydrated compound of 1,2-cyclohexanediaminplatinum(II)-bis-(4-methylbenzenesulfonate) is used instead of the dihydrate of 1,2-cyclohexanediaminplatinum(II)-bis-(4-methylbenzenesulfonate), the correction factor needs to be calculated accordingly.

Aside from the stability and ease of production, the application in targeted manner is crucial for antitumour agents. Pertinent polymer-modified platinum complexes are described in the prior art. Dinitrato(1,2-diaminocyclohexane)platinum(II) is used as starting material, for example, in US 2011/0286958 A1.

Surprisingly, it has been evident that the substance according to the invention, 1,2-cyclohexanediaminplatinum(II)-bis-(4-methylbenzenesulfonate) and hydrates thereof, can be used for producing polymer-bound cyclohexanediaminplatinum(II) complexes. The use according to the invention comprises:
a. providing 1,2-cyclohexanediaminplatinum(II)-bis-(4-methylbenzenesulfonate) or a hydrate thereof;
b. providing a polymer that comprises at least one or more groups capable of forming a bond to platinum;
c. reacting 1,2-cyclohexanediaminplatinum(II)-bis-(4-methylbenzenesulfonate) or a hydrate thereof and the polymer in a solvent.

Using 1,2-cyclohexanediaminplatinum(II)-bis-(4-methylbenzenesulfonate) or a hydrate thereof enables flexible reaction due to the high solubility of the products in water. The dihydrate, in particular, possesses high solubility in water of more than 80 mg/ml as compared to the compounds known from the prior art. Therefore, it is preferable to use the dihydrate of 1,2-cyclohexanediaminplatinum(II)-bis-(4-methylbenzenesulfonate) in step a. Neither the dihydrate, nor any of the other hydrates of 1,2-cyclohexanediaminplatinum(II)-bis-(4-methylbenzenesulfonate) according to the invention or said compound itself are inherently explosive substances. Accordingly, disadvantages resulting from the prior art are thus overcome. In this context, it is feasible to react 1,2- cyclohexanediaminplatinum(II)-bis-(4-methylbenzenesulfonate) or any of the hydrates thereof with known polymers. In this context, the platinum-bound tosylate or water groups act as leaving groups. These are substituted by groups within a polymer that is capable of forming a bond to platinum, preferably a coordinative bond.

The polymer bound to the cyclohexanediaminplatinum(II) complex preferably comprises a group that is capable of forming a 4- to 7-membered chelate ring with platinum. Pertinent chelate rings lead to a particular stable platinum(II) complex. In the scope of the present invention, 4- to 7-membered chelate rings comprise 4-membered, 5-membered, 6-membered, and 7-membered chelate rings.

Preferably, the polymer comprises carboxylate groups, amide groups or amino groups. Pertinent polymeric compounds are described and claimed, for example, in US 2011/0286958 A1.

The reaction of the cyclohexanediaminplatinum complex or hydrate thereof with the polymer proceeds in a solvent. The solvent preferably comprises water. Preferably, the solvent is water.

Preferably, the polymer is poly(N-(2-hydroxypropyl) methacrylamido-gly-gly-gly-diethylaminomalonate (poly (HPMA)-GGG-Ame), whereby gly represents glycyl.

In a particularly preferred embodiment, the present invention therefore relates to the use of the dihydrate of 1,2-cyclohexanediaminplatinum(II)-bis-(4-methylbenzenesulfonate) for producing polymer-bound cyclohexanediaminplatinum (II) complexes, comprising:
a. providing the dihydrate of 1,2-cyclohexanediaminplatinum(II)-bis-(4-methylbenzenesulfonate);
b. providing poly(HPMA)-GGG-Ame;
c. reacting the dihydrate of 1,2-cyclohexanediaminplatinum (II)-bis-(4-methylbenzolsulfonat) and poly(HPMA)-GGG-Ame in water.

The glycyl groups act as linkers in this context in order to enable more flexible attachment. The actual attachment of the polymer to platinum(II) is effected via the aminomalonate (Ame) group.

EXEMPLARY EMBODIMENTS

1. Chemical Synthesis of the Dihydrate of 1,2-Cyclohexanediaminplatinum(II)-bis-(4-Methylbenzenesulfonate)

For chemical synthesis of the dihydrate of 1,2-cyclohexanediaminplatinum(II)-bis-(4-methylbenzenesulfonate) (Pt (DACH)bis-tosylate), a suspension of dichloro-R,R-(1,2-diaminocyclohexane)platinum(II) was suspended in water and a solution containing 0.97 mol. equivalents of silver (p-toluenesulfonate) in water was added. The mixture was stirred in the dark at 55° C. for 48 hours. Subsequently, the suspension was cooled to 4° C. and kept stirring for another 4 hours. The resulting silver chloride was removed by filtration and the filtrate was then stirred in the presence of activated charcoal (5% by weight relative to the starting material) for another 20 hours at room temperature and then filtered again. The resulting filtrate was then reduced to 30% of its starting volume at 50° C. in a vacuum and then a slight excess of 1-butanol was added to the aqueous reaction mixture as an entrainer for complete removal of the water. This was attained by further reduction of the volume at 50° C. in a vacuum. To this water-free solution in 1-butanol, 15 eq. water, relative to platinum, were added and the solution was stirred for another 16 hours. The target compound was then precipitated by adding the anti-solvent, ethyl acetate, to the 1-butanol solution. The solid thus obtained was removed by filtration and dried at 40° C. in a vacuum.

Analysis of the compound revealed it to be the dihydrate (water content was detected to be 5.12%, theoretical water content is 5.24%).

The yields were between 60 and 85%.

2. Purification of the Dihydrate of 1,2-Cyclohexanediaminplatinum(II)-bis-(4-Methylbenzolsulfonat)

It was feasible to purify the dihydrate of 1,2-cyclohexanediaminplatinum(II)-bis-(4-methylbenzolsulfonat) in reproducible manner by subsequent re-crystallisation. For this purpose, the procedure described above under 1. was repeated: Dissolving in anhydrous 1-butanol, addition of defined quantities of water to form the dihydrate, precipitation through addition of ethyl acetate to the 1-butanol solution.

This yielded crystals of the dihydrate of 1,2-cyclohexanediaminplatinum(II)-bis-(4-methylbenzenesulfonate).

3. Production of a Diaqua Species

Pt(II)DACH-bistosylate (4.28 g; 6.568 mmol) was stirred in 45 ml of purified water at 50° C. for 1 h. The solution was then filtered through an 0.2 μm RC filter (nonwoven-reinforced) made by Sartorius and washed with 40 ml of purified water. The solution was allowed to cool to RT.

Figure 4:
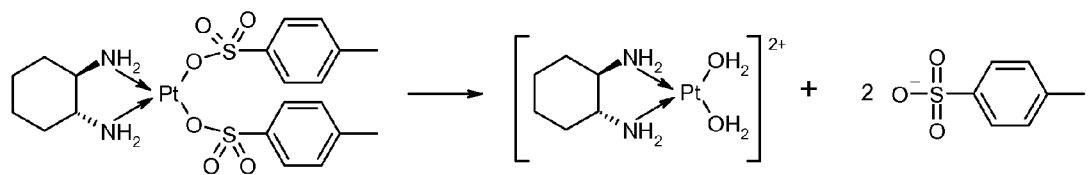
FIG. 4 is a scheme for production of a diaqua species starting from Pt(II)DACH-bistosylate.

The corresponding reaction is shown in FIG. 4.

4. Production of a Polymer Conjugate with Pt-DACH-Tosylate 11 g poly(HPMA)-GGG-Ame (equivalent to 5.5 mmol Ame) were placed in 62 ml purified water and stirred at RT for 30 min. Then, 5 ml 2 N aqueous NaOH solution were added (pH=13) and the batch was stirred for another 30 min at RT. The reaction solution was then adjusted to a pH of 7.4 with 5% aqueous $HNO_3$ solution, and then filtered through a P5 frit and then through Steritop (Merck; pore size 0.1 μm), and rinsed with 10 ml purified water. The filtrate was transferred to a flask and stirred strongly while the freshly prepared solution of the Pt-DACH-diaqua species (from example 3) was added, whereby the pH dropped to 5. The pH of the solution was then adjusted to 5.2 using 2 N aqueous NaOH solution. The solution was stirred at RT for 2 h at constant pH (the pH was re-adjusted according to need using NaOH solution). Then, the pH of the reaction solution was adjusted to 7.4 using 2 N aqueous NaOH solution and the batch heated to 38° C. and then stirred for 17 h at 38° C. at a constant pH of 7.4 (pH value was kept constant using a titrator (716 DMS Titrino made by Metrohm)). Subsequently, the solution was filtered through Steritop (Merck; 0.1 μm), and rinsed with 10 ml purified water. The solution was concentrated to approx. 60 ml by means of TFF and cleaned 5× with approx. 50 ml purified water. The retentate was then transferred to a double-walled flask and then 1.29 g NaCl, 243 mg $NaH_2PO_4*H_2O$, and 1.89 g $Na_2HPO_4*7H_2O$ were added. The solution was filled up with purified water to a total volume of 150 ml and, once the salts added were dissolved completely, the pH was adjusted to 7.4 with 2 N aqueous NaOH solution. The batch was heated to 38° C. and kept at this temperature for 4 h without stirring. Then the solution was filtered through Steritop (Merck; 0.1 μm) and the filtrate was concentrated to approx. 60 ml by means of TFF and rinsed with purified water (7 permeate solutions were collected). The retentate was then lyophilised.

The yield was 6.35 g (49.3%).
poly(HPMA)-GGG-Ame=poly(N-(2-hydroxypropyl)methacrylamido-gly-gly-gly-diethylaminomalonate
Poly(HPMA)=poly(N-(2-hydroxypropyl)methacrylamide
DACH=1R,2R-diaminocyclohexane
TFF=tangential flow filtration
RW=purified water
RT=room temperature (20° C.)

5. Comparison to the Prior Art 5.a Production of a Diaqua Species Starting from Pt-DACH-Nitrate (FIG. 5)

PtDACH(NO$_3$)$_2$ (10 g; 23.079 mmol) was placed in 149 ml purified water. A total of 657 μl of 5% HNO$_3$ were added and then stirred for 1 h at 70° C. The solution was then filtered through an 0.2 μm RC filter (nonwoven-reinforced) made by Sartorius and washed with 40 ml of purified water. The solution was allowed to cool to RT.

Figure 5:
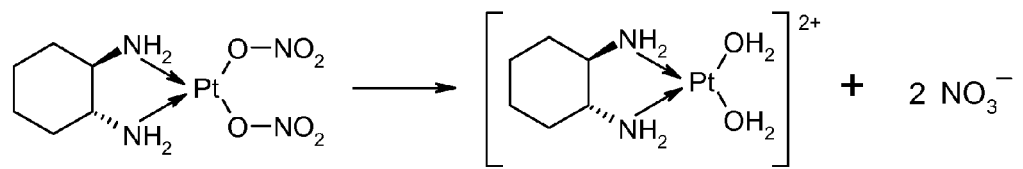
FIG. 5 is a scheme for production of a diaqua species starting from Pt-DACH-nitrate.

The corresponding reaction is shown in FIG. 5.

5.b. Production of a Polymer Conjugate with Pt-DACH-Nitrate

The production proceeded analogous to example 4, except that the diaqua species made from Pt-DACH nitrate, as produced in example 5.a was used in place of the diaqua species made from Pt-DACH-tosylate was used.

The yield was 7.13 g (66.8%).

The invention claimed is:

1. Dihydrate of 1,2-cyclohexanediaminplatinum(II)-bis-(4-methylbenzenesulfonate).

2. Method for producing the dihydrate of 1,2-cyclohexanediaminplatinum(II)-bis-(4-methyl-benzenesulfonate), comprising the following steps:
   a) reacting 1,2-cyclohexanediamindihalogenplatinum(II) and silver 4-methylbenzenesulfonate in a water-containing solvent to form 1,2-cyclohexanediaminplatinum(II)-bis-(4-methylbenzenesulfonate) and silver halogenide;
   b) separating the silver halogenide from the reaction mixture from step a);
   c) adding a compound that forms an azeotropic mixture with water;
   d) removing at least part of the water from the azeotropic mixture;
   e) adjusting the water fraction to form the dihydrate of 1,2-cyclohexanediaminplatinum(II)-bis-(4-methylbenzenesulfonate);
   f) isolating the dihydrate of 1,2-cyclohexanediaminplatinum(II)-bis-(4-methylbenzenesulfonate).

3. Method according to claim 2, wherein chlorine, bromine and/or iodine is used as halogen in 1,2-cyclohexanediamindihalogenplatinum(II).

4. Method according to claim 2, wherein the reaction proceeds at sub-stoichiometric levels of silver 4-methylbenzenesulfonate.

5. Method according to claim 2, wherein activated charcoal is added to the reaction mixture in step c) after separation of the silver halogenide in step b) and before the addition of the compound that forms an azeotropic mixture with water.

6. Method according to claim 2, wherein the water-containing solvent in step a) is water or a mixture containing water and at least one further compound that forms an azeotropic mixture with water.

7. Method according to claim 2, wherein the compound that forms an azeotropic mixture with water is n-butanol.

8. Method according to claim 2, wherein the azeotropic mixture is fully removed in step d) while forming a solution of 1,2-cyclohexanediaminplatinum(II)-bis-(4-methylbenzenesulfonate) in the compound that forms an azeotropic mixture with water.

9. Method of using the dihydrate of 1,2-cyclohexanediaminplatinum(II)-bis-(4-methylbenzenesulfonate) as reference standard for (SP-4-2)-diaqua[(1R,2R)-cyclohexane-1,2-diamin-κN, κN']platinum, comprising
   i. providing an oxaliplatin solution;
   ii. providing a solution of the dihydrate of 1,2-cyclohexanediaminplatinum(II)-bis-(4-methylbenzenesulfonate) as reference standard;
   iii. recording a chromatogram of the oxaliplatin solution from step i);
   iv. recording a chromatogram of the reference standard solution from step ii); and
   v. comparing the chromatograms from steps iii) and iv) in order to determine the fraction of (SP-4-2)-diaqua[(1R,2R)-cyclohexane-1,2-diamin-κN, κN']platinum.

10. Method according to claim 9, wherein an aqueous solution is used in step i) and/or step ii).

11. Method according claim 9, wherein the chromatograms in steps iii) and iv) are chromatograms from high-pressure liquid chromatography (HPLC).

12. Method of using the dihydrate of 1,2-cyclohexanediaminplatinum(II)-bis-(4-methylbenzenesulfonate) for producing polymer-bound cyclohexanediaminplatinum(II) complexes, comprising:
   a. providing the dihydrate of 1,2-cyclohexanediaminplatinum(II)-bis-(4-methylbenzenesulfonate);
   b. providing a polymer that comprises at least one or more groups capable of forming a bond to platinum;
   c. reacting the dihydrate of 1,2-cyclohexanediaminplatinum(II)-bis-(4-methylbenzenesulfonate) and the polymer in a solvent.

13. Method according to claim 12, wherein the polymer comprises a group that is capable of forming a 4- to 7-membered chelate ring with platinum.

14. Method according to claim 12, wherein the polymer comprises carboxylate groups, amide groups or amino groups.

15. Method according to claim 12, wherein the solvent comprises water.

* * * * *